United States Patent [19]

Hanke

[11] 4,247,582

[45] Jan. 27, 1981

[54] ADHESIVE SPLICING TAPE

[75] Inventor: Rudolf Hanke, Monheim, Fed. Rep. of Germany

[73] Assignee: Hama Hamaphot K.G. Hanke & Thomas, Monheim, Fed. Rep. of Germany

[21] Appl. No.: 714,766

[22] Filed: Aug. 16, 1976

[30] Foreign Application Priority Data

Nov. 8, 1975 [DE] Fed. Rep. of Germany ....... 2550259

[51] Int. Cl.[2] ...................... A61F 13/02; B65D 65/28; G09F 3/00

[52] U.S. Cl. ....................................... 428/43; 428/41; 428/124; 428/134; 428/137

[58] Field of Search .................. 427/207, 208; 428/12, 428/57-62, 41, 43, 131-134, 137, 124, 260-269, 343-356

[56] References Cited

U.S. PATENT DOCUMENTS

| | | | |
|---|---|---|---|
| 2,049,030 | 7/1936 | Strauss | 427/207 X |
| 2,895,865 | 7/1959 | Humphner | 428/43 X |
| 3,076,588 | 2/1963 | Conway et al. | 427/207 X |
| 3,136,678 | 6/1964 | Herzig | 156/157 X |
| 3,475,263 | 10/1969 | Kapilow et al. | 428/61 X |
| 4,041,201 | 8/1977 | Wurker | 156/157 X |

*Primary Examiner*—Bernard D. Pianalto
*Attorney, Agent, or Firm*—Ross, Ross & Flavin

[57] ABSTRACT

Adhesive splicing tape, for cinematographic film, of the type having apertures for registering with the film sprocket holes and adapted to be folded in hairpin fashion about respective one edges of film portions to be spliced, has a central portion thereof, which would normally embrace the said one edges and overlie a sound track there-adjacent, readily detachable to enable it to be removed after a joint has been made to leave the sound track uncovered and to leave the said one edges uninterrupted.

1 Claim, 10 Drawing Figures

FIG. 1
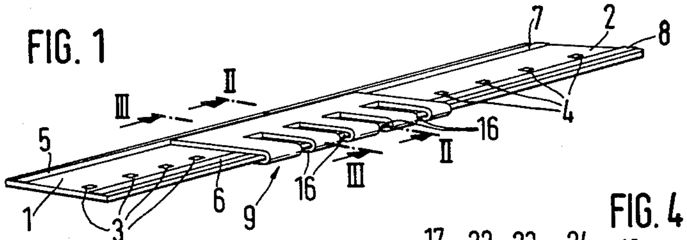
FIG. 4
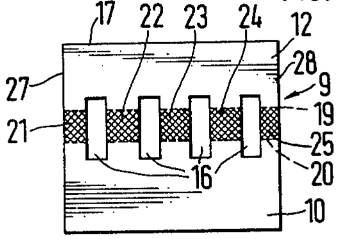
FIG. 2
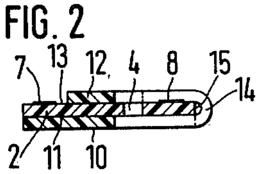
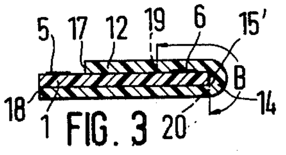
FIG. 3
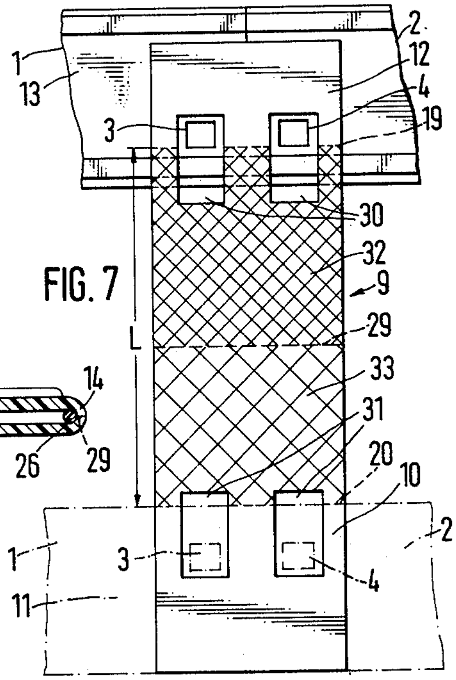
FIG. 7
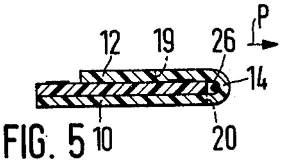
FIG. 5
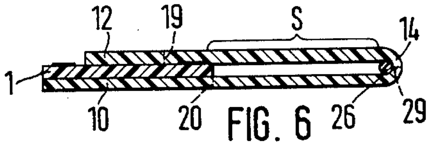
FIG. 6
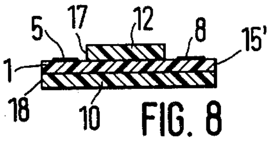
FIG. 8

ADHESIVE SPLICING TAPE

BACKGROUND OF THE INVENTION

This invention relates to adhesive splicing tape, for cinematographic film, having sprocket holes and a magnetic sound track, of the type hereinafter referred to as "of the type described", having apertures for registering with the sprocket holes and adapted to be folded in hairpin fashion about respective one edges of the film portions to be spliced.

DESCRIPTION OF THE PRIOR ART

It is known to connect portions of cinematographic film, for example 8 mm films, by means of a tape of the type described. The ends of the film portions are butt jointed and held together by the tape which adheres with its one adhesive coated limb to the top side of the film and with its other adhesive coated limb to the underside of the film portion, its centre portion embracing respective one edges of the film portions.

Portions of film provided with sound tracks are connected together in this manner. With such a mode of connection, the sound track is interrupted at the joint. This has the effect, when the film is projected, of causing noise. This noise, which is undesirable, arises when the joint travels under the sound reproducing head. Added to this is the fact that when the centre portion of the tape encounters a guide in the projector, the film is deflected sideways from its line of travel. This is noticeable on the screen and is also undesirable.

OBJECT OF THE INVENTION

An object of the present invention is to provide an adhesive splicing tape, of the type described, whereby joints can be made which do not have the above described undesirable features.

BRIEF DESCRIPTION OF THE INVENTION

The invention provides an adhesive splicing tape of the type described, wherein a central portion of the tape, which would normally embrace respective one edges of portions of film to be joined and any magnetic sound track adjacent those edges, it detachably fastened to the remainder of the tape to enable it to be removed after a joint has been made.

The central portion can be rendered detachable by a line or lines of weakening of the material of the tape.

The or each line of weakening can be a line of perforations, a crease line, or a score line which facilitates detaching of the central portion by tearing.

In use of the tape of the invention, joining the film portions is undertaken in the previously known manner and subsequently the respective one edges of the film portions and the sound track adjacent these edges, which have been covered by the tape, are exposed. For this purpose, it is sufficient to detach the central portion of the tape, which embraces the one edge portions which masks the sound track, from the rest of the tape.

In order to prevent adhesion of the tape in its central area this central area, can be left uncoated with adhesive.

Advantageously, the separating line of the tape which lies on the reverse side of the film is such as to coincide with the edge of the film, whereas that on the emulsion side of the film coincides with or is clear of the edge of the sound track remote from the said one edge portions. The upper limb of the tape is preferably so dimensioned that it does not overly any sound track adjacent the opposite edges of the film portions.

In order to simplify still further the detachment of the central part of the tape, it is advantageous if a tear-off element is provided between the limbs at the bend in the tape. This element, which can be a thread or a wire, is preferably arranged to be longer than the tape and to have protruding end portions. With such a design, the application of a comparatively slight tractive force to the tear-off element is sufficient to release easily the central detachable portion of the tape.

It is also favourable if the limbs of the tape, which are bent in hairpin fashion, are lengthened adjacent the bend to form extensions which can be readily gripped.

It can furthermore be advantageous if the tape can be torn apart along the bend, for example by having perforations therealong.

BRIEF DESCRIPTION OF THE DRAWINGS

The invention will be described further, by way of example, with reference to the accompanying drawings, wherein:

FIG. 1 is a perspective view of a pair of film portions joined by a length of tape of the invention, before separation of a detachable central portion thereof;

FIG. 2 is a section along the line II—II in FIG. 1;

FIG. 3 is a section taken along the line III—III in FIG. 1;

FIG. 4 shows the splicing tape shown in FIG. 1 in an opened-out condition;

FIG. 5 is a view similar to that of FIG. 3, but in which at the bend of the tape between its limbs a tear-off element is provided;

FIG. 6 is a section, corresponding to FIG. 5, through a tape having an extension;

FIG. 7 shows the tape of FIG. 6 in an opened-out condition;

FIG. 8 is a section taken along the line III—III in FIG. 1 after detachment of the central part of the tape;

DESCRIPTION OF A PERFERRED EMBODIMENT

Figure 9:
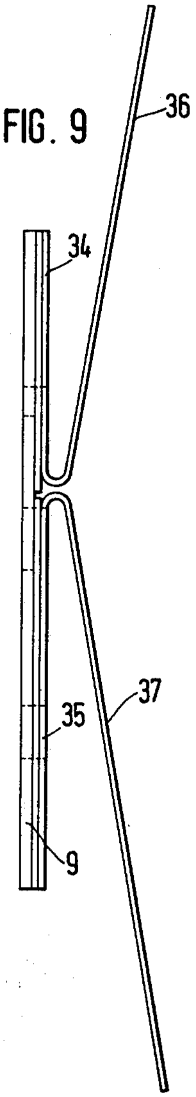
FIG. 9 is a front view of a label, tab or ticket having carrier papers folded in hairpin fashion, and carrying splicing tape of the present invention.

A pair of film portions 1 and 2 are butt jointed. They have sprocket holes 3 and 4. Moreover, they are provided with sound tracks 5, 6 and 7, 8. The portions 1, 2 are connected together by means of a splicing tape 9 of the present invention. The tape 9 is folded in hairpin fashion and butts with a lower limb 10 against the underside 11 of the film portion 1, 2 and with an upper limb 12 against the upper side 13 of the film portions 1, 2. The hairpin bend 14 embraces one edge 15 or 15' respectively of the film portion 1, 2.

The tape in accordance with FIGS. 1 to 4 has four recesses 16, which extend over the entire bend 14 and extend so far into the limbs 10, 12 that the sprocket holes 3 or 4 respectively are fully freely accessible when the tape is adhered to the portions 1, 2 in the manner evident from FIGS. 1 to 4.

Provided in the tape 9 are separation lines 19, 20 which extend parallel to the marginal edges 17, 18 thereof. These separation points are lines of weakening achieved, for example by perforations in the tape. However, they could also be formed by crease lines or score lines. Because of these lines 19, 20, the cross-hatched pieces 21, 22, 23 24, 25 (which constitute a detachable central portion of the tape) can be severed relatively easily from the rest of the tape 9. The line 19 is so placed that it extends behind the masked sound track 8 on the other side of the bend 14, whereas the line 20 is so arranged that it comes to rest, on the underside of the portions 1, 2, along the edges 15, 15'.

The upper limb 12 is of such a length that the sound track 5 or 7 respectively on the side opposite the bend 14 is freely accessible.

In order to simplify still further the removal of the pieces 21 to 25, in the case of the design in accordance with FIG. 5 there is inserted between the limbs 10, 12 at the bend 14 a tear-off element 26, which overlaps somewhat the marginal sides 27, 28. The tear-off element 26 can for example be a thread or a wire. When a tractive force in the direction of the arrow P is applied to the tear-off element 26 by grasping of the overlapping ends the parts 21 to 25 are easily detached. After detaching the parts 21 to 25, the guide edges 15 or 15' respectively of the films 1, 2 in the same way as all the sound tracks are fully freely accessible, as is evident from FIG. 8.

In the version of the tape in accordance with FIG. 6, the limbs 10 and 12 are lengthened on the side of the bend 14 by a portion S. With this extension S these limbs 10, 12 overlap the edges 15 or 15', facing the bend. They form with this extension a grip which can easily be grasped by hand, so that the central portion that is to be detached from the tape can easily be removed.

Also in the version of FIG. 6 a tear-off element 26 can be used. This could even be incorporated by being fixed in an adhesive press. In this case the tape would have to be such as to be able to be torn open or pulled apart along the bend 14. For this purpose a line or perforations 29 could be situated in the bend 14.

The tape in accordance with FIG. 6 is, as is evident from FIG. 7, provided with two recesses in the limb 10 and two in the limb 12. These recesses are designated by numerals 30 and 31. In the position evident from FIG. 6 the tape 9 is so arranged that the recesses 30 leave completely free the sprocket holes 3 and 4 both on the picture side and on the reverse side of the film portions 1, 2.

As soon as the perforation 29 is undone, the tabs 32 and 33 can be grasped and be drawn off from the perforations 19 and 20.

Figure 10:
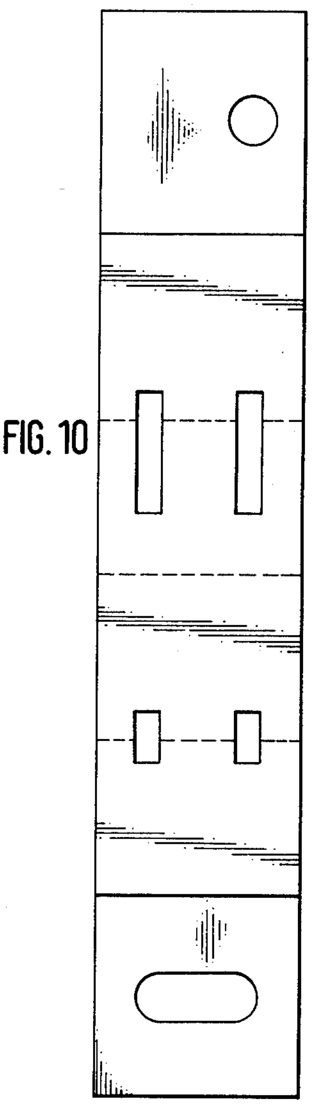
FIG. 10 shows the label of FIG. 9, in plan view.

Until the tape 9 is used, it can be mounted on the short limbs 34 and 35 of two strips 36 and 37 of a carrier paper folded in hairpin fashion, as is evident from FIGS. 9 and 10.

It is additionally of advantage if the tape is kept free from adhesive between the lines 19 and 20. In the version in accordance with FIGS. 1 to 5, the tape 9 would be free from adhesive along the loop B. In a corresponding manner the tape 9 would have to be kept free from adhesive along the section L (FIG. 7).

I claim:

1. A splicing tape for splicing together a pair of film sections arranged in end-to-end aligned butting relationship with each section having a row of regularly-spaced sprocket holes and a longitudinally-extending sound track comprising:

a unitary blank including oppositely-facing upper and lower leaves each having an adhesive coating on one face thereof for adherence to the opposite respective gloss and coat sides of the to-be-spliced film sections adjacent butting ends thereof, and a connecting tearable leaf disposed between the upper and lower leaves with a tear line serving as the line of connection between the tearable leaf and each adjacent of the upper and lower leaves, each of the leaves having apertures for registering with the film sprocket holes, the blank being first foldable in hairpin fashion around the butting ends of and with the apertures in register with the sprocket holes of the to-be-spliced film sections for effecting adherance of the upper and lower leaves to the adjacent end portions of the gloss and coat sides of the to-be-spliced film sections, and the tearable leaf being then removable by tearing along the tear lines with the leaves remaining in adhered positions and exposing the aligned end portions of the sound tracks.

* * * * *